United States Patent [19]
von der Heyde

[11] Patent Number: 5,914,062
[45] Date of Patent: Jun. 22, 1999

[54] TICK REMOVAL DEVICE

[76] Inventor: Christian P. von der Heyde, 182 Great Hill Rd. Ext., East Sandwich, Mass. 02537

[21] Appl. No.: 09/097,402

[22] Filed: Jun. 15, 1998

[51] Int. Cl.$^6$ .............................. H05B 1/00; A61B 17/50
[52] U.S. Cl. .......................... 219/227; 43/134; 294/99.2; 294/100; 606/28; 606/210
[58] Field of Search .................. 219/227–231, 219/233, 243; 606/210, 211, 51, 52, 205, 206, 28–31, 45; 294/99.2, 93–94, 100, 119.1, 166, 168; 43/134, 135; 83/15, 16, 170, 171

[56] References Cited

U.S. PATENT DOCUMENTS

| | | | |
|---|---|---|---|
| 3,200,028 | 8/1965 | Chisholm | 219/227 |
| 3,654,427 | 4/1972 | Schoenwald | 219/85.16 |
| 3,844,291 | 10/1974 | Moen | 606/206 |
| 3,938,527 | 2/1976 | Rioux et al. | 606/133 |
| 4,155,164 | 5/1979 | White | 433/3 |
| 4,213,460 | 7/1980 | Weiner | 606/131 |
| 4,240,435 | 12/1980 | Yazawa et al. | 606/133 |
| 4,303,268 | 12/1981 | Davidson | 294/99.2 |
| 4,393,872 | 7/1983 | Reznik et al. | 604/264 |
| 4,442,837 | 4/1984 | Keatley | 606/131 |
| 4,850,108 | 7/1989 | Perrino et al. | 30/90.4 |
| 4,979,771 | 12/1990 | Childs, III | 294/99.2 |
| 5,002,323 | 3/1991 | Idsund | 294/100 |
| 5,035,695 | 7/1991 | Weber, Jr. et al. | 606/42 |
| 5,142,117 | 8/1992 | Hoggatt et al. | 219/85.16 |
| 5,250,046 | 10/1993 | Lee | 606/29 |
| 5,276,306 | 1/1994 | Huffman | 219/229 |
| 5,376,087 | 12/1994 | Haber et al. | 606/27 |
| 5,407,243 | 4/1995 | Riemann | 294/100 |
| 5,556,563 | 9/1996 | Heyde et al. | 219/227 |
| 5,565,122 | 10/1996 | Zinnbauer et al. | 219/227 |
| 5,690,847 | 11/1997 | LaValley et al. | 219/233 |

FOREIGN PATENT DOCUMENTS

| | | |
|---|---|---|
| 3002088 | 7/1981 | Germany. |
| 3624250 | 2/1988 | Germany. |
| 628792 | 3/1982 | Switzerland. |

*Primary Examiner*—Teresa Walberg
*Assistant Examiner*—Vinod D. Patel
*Attorney, Agent, or Firm*—William Nitkin

[57] ABSTRACT

A device for removing a tick attached to a host, such device having a tweezer with first and second tweezer arms disposed on a slide member movable within an outer casing, such tweezer arms movable within first and second channels defined on the inside of the outer casing with the front tips of the tweezer arms extendible and retractable through an opening in the front of the outer casing, with the channels tapering inwardly to compress and force the tips of the tweezer arms together as they pass through the opening to grasp a tick. A power source is provided in the rear of the slide member which can be a battery disposed within a chamber in the slide member and interconnected through a manually controlled switch to a heat member. An electrical circuit is completed by manually activating the switch when the tweezer arms are in their forward advanced position extending out the opening of the casing to provide heat to a heating member tip adjacent to the tweezer arms and the tick grasped therebetween to cause the tick to release its grip. The tick is then pulled away from the host with the tweezer arms.

2 Claims, 3 Drawing Sheets

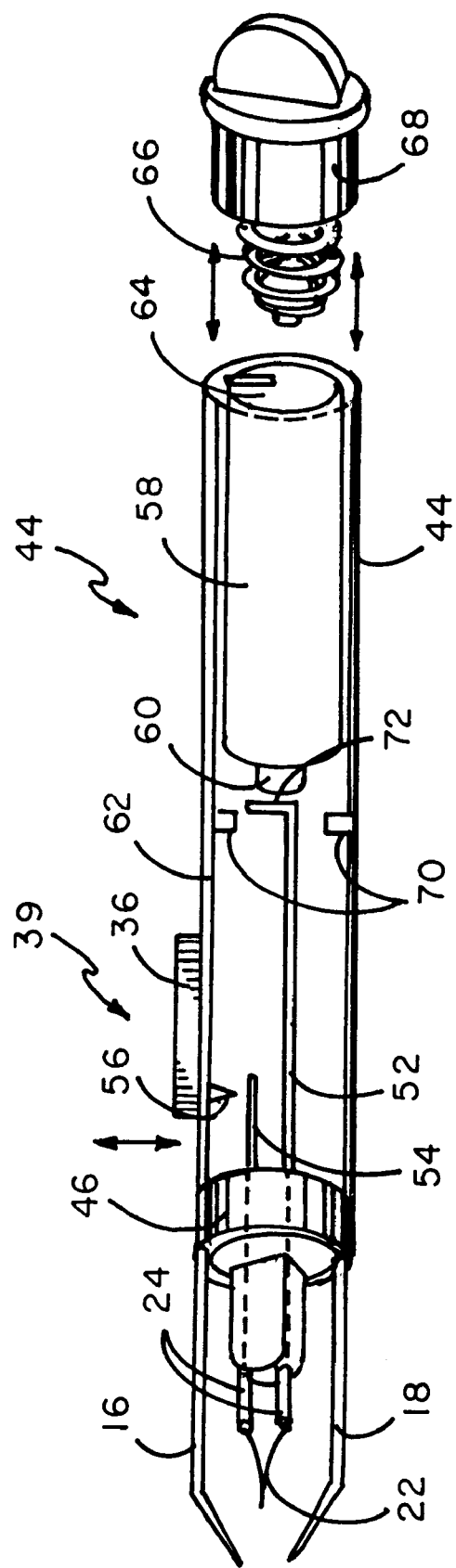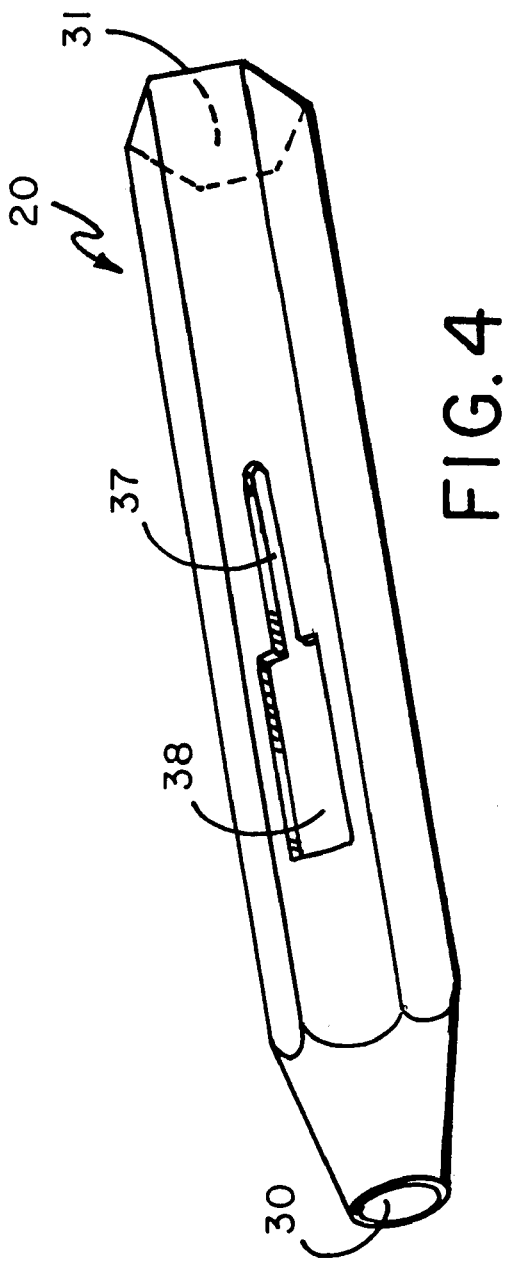

TICK REMOVAL DEVICE

BACKGROUND OF THE INVENTION

1. Field of the Invention

The device of this invention resides in the area of devices for removing ticks from animals and people and more particularly relates to extendible and retractable tweezers disposed in a casing which tweezer, upon manually guided extension, grips the tick. The device then provides sufficient heat near the tick to cause the tick to release its grip, allowing the user to pull the tick off the host by the tweezers.

2. Description of the Prior Art

There are many hand tools which use tweezer-like elements for removing a tick from the skin of an animal. For example, U.S. Pat. No. 4,213,460 to Weiner discloses forceps with an electrical current passing therethrough to provide heat with the forceps having oppositely aligned cup-shaped members to surround and remove the tick. U.S. Pat. No. 4,979,771 to Childs, III also discloses the use of cup members at the end of tweezer-like elements to surround the tick. U.S. Pat. No. 5,276,306 to Huffman teaches the use of a heated needle which, when poked into the tick, causes the tick to release its grip, and the tick can then be scooped off the skin by a spoon member disposed below the needle. U.S. Pat. No. 5,556,563 to Applicant and Michael E. Backus teaches tweezer arms which move within channels and when the tweezer arms are heated and advanced forward, they move together to grasp and heat the tick, causing it to release its grip on its host.

SUMMARY OF THE INVENTION

It is an object of this invention to provide a convenient and effective device to remove a tick attached to the skin of a host, such as an animal or person, such device incorporating tweezers and which device utilizes an internal battery as a source of power to provide heat near the tick to cause such tick discomfort and causing it to release its grip in order to escape the heat. In the tick removal device of this invention the tweezer arms are disposed within a casing such that the tweezer arms are manually slid forward within inwardly tapered channels formed on the interior of the casing. The tweezer arms are disposed such that as they pass through an opening in the front of the casing, the tweezer arms are forced and compressed toward one another by the shape of the channels to grasp the tick. As the tweezer arms come together and close on the tick, a heat element is positioned adjacent to the tick which heats the tick to cause it to release its grip on the host.

BRIEF DESCRIPTION OF THE DRAWINGS

FIG. 3 illustrates a side view of the inner slide member.

FIG. 4 illustrates a perspective view of the outer casing.

DESCRIPTION OF THE PREFERRED EMBODIMENT(S)

Figure 1:
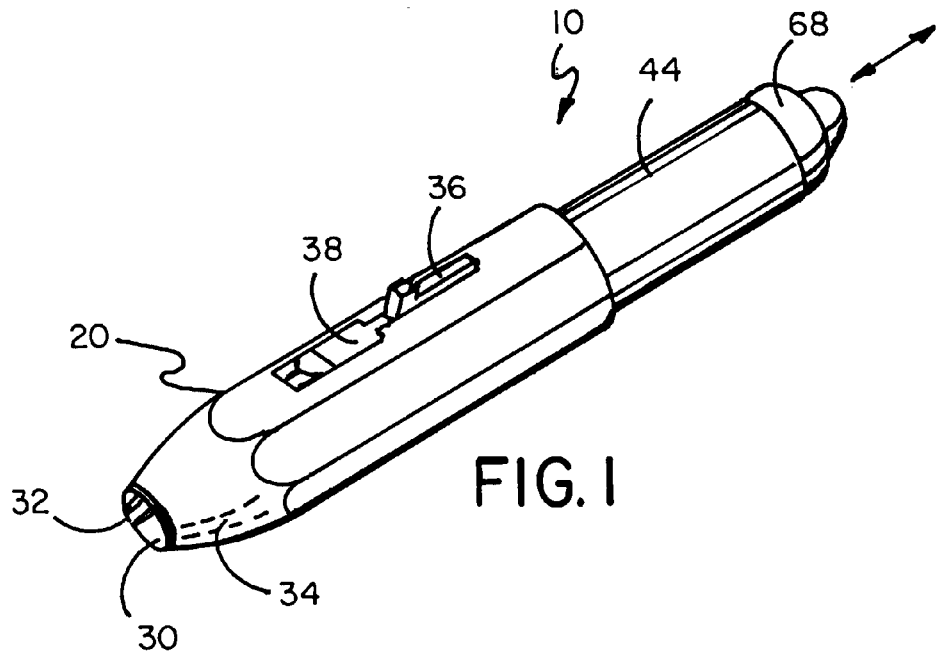
FIG. 1 illustrates a front perspective view of the device of this invention with the pointed tips of the tweezers in a retracted position.
Figure 2:
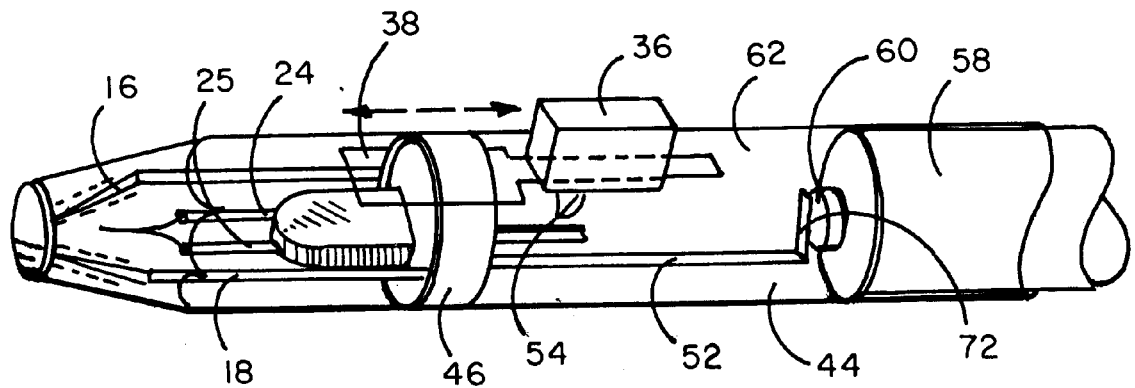
FIG. 2 illustrates a perspective partial view of the interior of the device.

FIG. 1 illustrates a perspective view of the tick removal device 10 of this invention. The device has two main parts: an outer casing 20 and an inner slide member 44 which slides back and forth, as maneuvered by the user, within outer casing 20. Outer casing 20, as seen in FIG. 4, has a front opening 30, a rear opening 31 and on its top has an elongated slot 37 which at the front portion thereof opens to form a switch depression aperture 38. Slide member 44, as seen in FIG. 3, has first and second tweezer arms 16 and 18 extending at the front thereof from a collar 46. First and second tweezer arms 16 and 18 can be made of metal and can, in one embodiment, be formed from one piece of metal with collar 46 being part of the same metal piece. The tweezer arms at their front first ends bend inward toward one another and at their rear second ends are part of, or attached to, collar 46. Collar 46 fits around the front portion of slide member 44. Disposed between first and second tweezer arms 16 and 18 is heating member tip 22 which is disposed somewhat to the rear of the first ends of first and second tweezer arms 16 and 18. Heating member tip 22 is attached by electrodes 24 which extend rearwards to form first electrode contact 52 and second electrode contact 54. At the rear of slide member 44 is a battery chamber defined by battery stop member 70 into which chamber battery 58 is positioned and held in place by attaching rear cap 68 to the rear opening of slide member 44. Cap 68 can have a metal spring 66 protruding therefrom to apply forward pressure onto battery 58 and to aid in making electrical contact with the second pole 64 of battery 58. The cap can be held in place by traditional means such as screw threads or by the engagement of pin portions of the cap inserted into slots designed, upon rotation of the cap, to retain such pins. An electrical line 62 extends from the second pole 64 of battery 58 forward to a button contact member 56. Button contact member 56 is positioned on the bottom of button 36 forming switch 39. Switch 39 is activated when button 36 is depressed, causing button contact 56 to touch and make electrical contact with second electrode contact 54, thus completing an electrical circuit between heating member tip 22 and battery 58 such that when button 36 is depressed when it has been moved forward over switch depression aperture 38, heating member tip 22 heats up. When slide member 44 is inserted into the rear opening 31 of the outer casing and slid forward, button 36 can be engaged in slot 37 such that manual movement of button 36 within slot 37 will move slide member 44 forward within outer casing 20. When button 36 has moved within slot 37 from the narrow sides of the slot which prevent it from being depressed to a position over the area of switch depression aperture 38, button 36 can then be depressed, completing the electrical circuit to cause heat to be generated in heating member tip 22.

Figure 6:
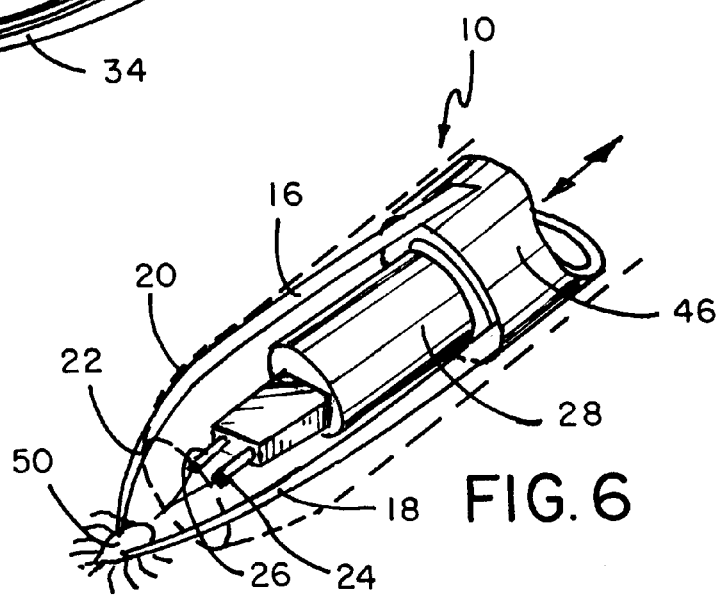
FIG. 6 illustrates a perspective see-through view through the front of the tick removal device of this invention with the tweezer arms in their extended position.

At the front of outer casing 20 the casing tapers inward to front opening 30. Within this tapered portion are defined first and second channels 32 and 34 within which first and second tweezer arms 16 and 18, respectively, travel. The inward tapering and shape of outer casing 20 and first and second channels 32 and 34 cause the first ends of first and second tweezer arms 16 and 18 to be compressed to move closer together as slide member 44 is advanced forward within outer casing 20 by the manual forward advancement of button 36 within slot 37. As seen in FIG. 6, when fully advanced forward the first ends of first and second tweezer arms 16 and 18 come together and as they come together the device of this invention can be manipulated to grasp tick 50.

At the same time the user can depress button 36 within switch depression aperture 38, completing an electrical circuit to heating member tip 22 which heating member tip is adjacent to the tick. The heat in such close proximity to the tick causes the tick discomfort, and it releases its grip of its mouth parts on the host person or animal to which it is attached. The tick can then be easily removed as it is then grasped tightly by the first ends of first and second tweezer arms 16 and 18.

Figure 7:
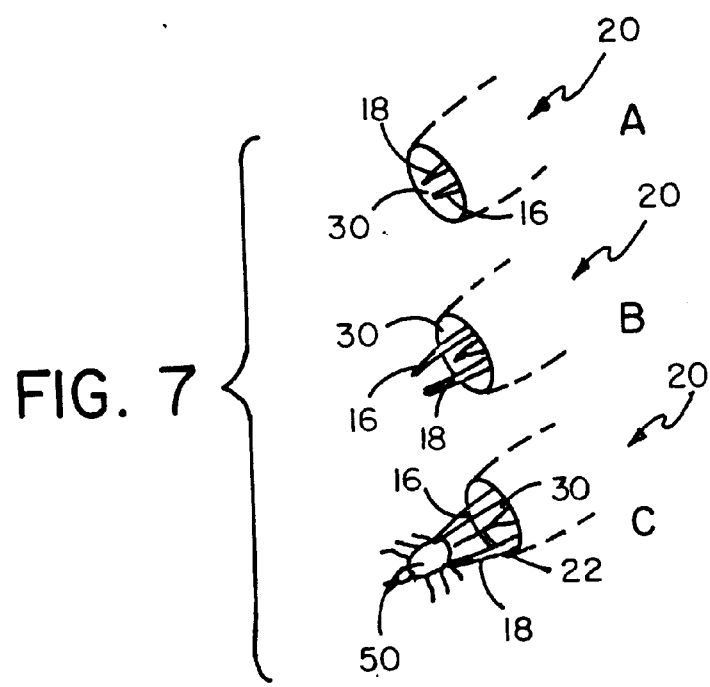
FIG. 7 illustrates three front perspective views of the front of the device, showing the tweezer arms emerging from the front of the device to grasp a tick.

FIG. 7 illustrates the forward progression of first and second tweezer arms 16 and 18 as they extend out of casing 20.

Figure 5:
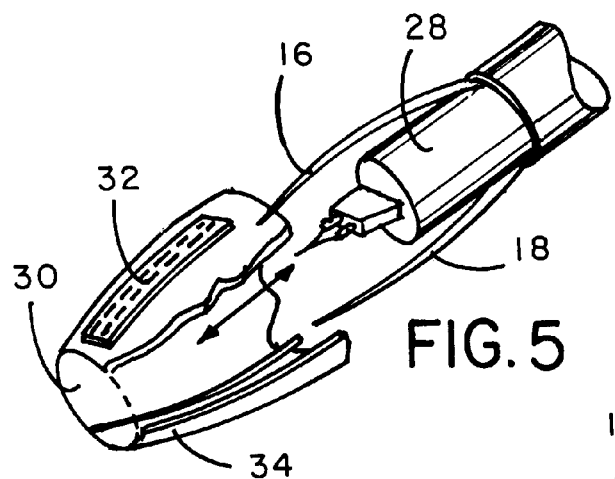
FIG. 5 illustrates a perspective see-through view through the front of the tick removal device of this invention.

FIG. 5 illustrates first and second channels 32 and 34 formed on the inside of the front of casing 20 which channels direct and cause the inward movement of first and second tweezer arms 16 and 18 when slide member 44 is advanced forward within outer casing 20. The separation of the heating member tip from the tweezer members aids in causing the natural release by the tick of its mouth parts from the person or animal it is biting. It is critical that not too high a temperature is produced in order to avoid killing the tick. If the tick were killed by the heat, its mouth parts would remain closed and it would be very difficult to remove the entire tick from its host. By having the heat separated from the tweezer arms and disposed to the rear of the tick, the tweezer arms merely perform a grasping function and do not kill the tick. The tick is then discomforted sufficiently by the heat of the non-contacting heating member tip that it releases its bite in an attempt to escape from the heat. Other equivalent heating sources other than the electrical wire of heating member tip 22 can be utilized with the same type of structure as illustrated, such as a high intensity light bulb which puts out heat.

Although the present invention has been described with reference to particular embodiments, it will be apparent to those skilled in the art that variations and modifications can be substituted therefor without departing from the principles and spirit of the invention.

I claim:

1. A device for the removal of a tick attached to a host animal or person, comprising:

an outer casing having an inwardly tapering front end, a rear end and an interior cavity defined therein, said casing having an exterior wall, an interior wall and openings defined in said casing at said front end and said rear end;

first and second channels defined in said interior wall of said front end of said casing disposed opposite to one another and tapering inwardly toward one another;

a slide member having a front end and a rear end;

first and second tweezer arms, each having a forwardly disposed first end and a rearwardly disposed second end, said second end of each tweezer arm attached to said front end of said slide member, said first and second tweezer arms extending from said front end of said slide member toward said front end of said casing; said first and second tweezer arms disposed, respectively, within said first and second channels in said outer casing;

means to move said slide member within said casing, said slide member in its use mode adapted to be moved in said casing from a first rearward position to a second forward position to advance said first and second tweezer arms within said first and second channels out said opening at said front end of said casing where said first and second tweezer arms are moved closer toward one another by compression contact with said tapering channels by said forward movement within said first and second channels as said first and second tweezer arms extend out said front end of said outer casing to grasp said tick, and in its storage mode to be moved rearward from its second forward position to its first rearward position where said first and second tweezer arms no longer are compressed by said tapered channels and move back apart from one another;

means to provide heat from a heat source not located in said first and second tweezer arms, said heat source disposed adjacent to said tick such that when said first and second tweezer arms are in their second forward position sufficient heat is provided to cause said tick to release its grip on said host when said tick is grasped by said first ends of said first and second tweezer arms said means to provide heat comprising a centrally disposed heat-producing member located between said first and second tweezer arms, said heat-producing member disposed a distance to the rear of said first ends of said first and second tweezer arms, said heat-producing member disposed at said front end of said slide member;

means to provide power to said heat-producing member when desired; and said means to move said slide member comprising a button member extending from said slide member, said outer casing having a slot defined therein, said slot having a front portion and a rear portion said button member manually movable in said slot of said outer casing so as to move said slide member from its first rearward position to its second forward position to cause said first and second tweezer arms to grasp said tick, said button member further including means, when depressed, to direct power to said heat-producing member to heat said tick sufficiently to cause said tick to release its grip on said host.

2. A device for the removal of a tick attached to a host animal or person, comprising:

an outer casing having an inwardly tapering front end, a rear end and an interior cavity defined therein, said casing having an exterior wall, an interior wall and openings defined in said casing at said front end and said rear end;

first and second channels defined in said interior wall of said front end of said casing disposed opposite to one another and tapering inwardly toward one another;

a slide member having a front end and a rear end;

first and second tweezer arms, each having a forwardly disposed first end and a rearwardly disposed second end, said second end of each tweezer arm attached to said front end of said slide member, said first and second tweezer arms disposed, respectively, within said first and second channels in said outer casing;

means to move said slide member within said casing, said slide member in its use mode adapted to be moved in said casing from a first rearward position to a second forward position to advance said first and second tweezer arms within said first and second channels out said opening at said front end of said casing where said first and second tweezer arms are moved closer toward one another by compression contact with said tapering channels by said forward movement within said first and second channels as said first and second tweezer arms extend out said front end of said outer casing to grasp said tick and in its storage mode to be moved rearward from its second forward position to its first rearward position where said first and second tweezer arms no longer are compressed by said tapered channels and move back apart from one another, means to provide heat from a heat source not located in said first and second tweezer arms, said heat source disposed adjacent to said tick such that when said first and second tweezer arms are in their second forward position sufficient to cause said tick to release its grip on said host when said tick is grasped by said first ends of said first and second tweezer arms;

said means to provide heat further including:

a centrally disposed heat member located between said first and second tweezer arms and at a distance to the rear of said first ends of said first and second tweezer arms;

wherein said means to provide heat are positioned at the front end of said slide member, said slide member further including means to provide power to said means to provide heat;

said means to move said slide member comprising a button member extending from said slide member, said outer casing having a slot defined therein, said slot having a front portion and a rear portion, said button member manually movable in said slot of said outer casing so as to move said slide member from its first rearward position to its second forward position;

said button member further including means to activate an electrical switch; and wherein said slot in said outer casing at its front portion has a button receipt aperture defined therein, allowing said button member to be slid within said front portion of said slot and then manually depressed in said button receipt aperture to activate said electrical switch to provide power to said heat member when said first and second tweezer arms are in their second forward position.

* * * * *